United States Patent
Plicchi et al.

(10) Patent No.: US 6,620,139 B1
(45) Date of Patent: Sep. 16, 2003

(54) CATHETER SYSTEM FOR PERFORMING INTRAMYOCARDIAC THERAPEUTIC TREATMENT

(75) Inventors: Gianni Plicchi, Bologna (IT); Tonino Bombardini, Imola (IT); Emanuela Marcelli, Macerata (IT)

(73) Assignee: Tre Esse Progettazione Biomedica S.r.l., Bologna (IT)

( * ) Notice: Subject to any disclaimer, the term of this patent is extended or adjusted under 35 U.S.C. 154(b) by 0 days.

(21) Appl. No.: 09/831,493
(22) PCT Filed: Nov. 11, 1999
(86) PCT No.: PCT/EP99/08686
§ 371 (c)(1), (2), (4) Date: May 10, 2001
(87) PCT Pub. No.: WO00/35531
PCT Pub. Date: Jun. 22, 2000

(30) Foreign Application Priority Data

Dec. 14, 1998 (IT) .......................... BO98A0691
Feb. 5, 1999 (IT) .......................... BO99A0050

(51) Int. Cl.$^7$ ...................... A61M 25/00; A61M 29/00; A61M 1/00
(52) U.S. Cl. ...................... 604/264; 604/28; 604/103.1
(58) Field of Search ...................... 606/53, 159, 170, 606/471, 41; 424/93.2; 604/272, 264, 22, 66, 28, 21; 600/564; 128/878

(56) References Cited

U.S. PATENT DOCUMENTS

| | | | |
|---|---|---|---|
| 5,300,022 A | * 4/1994 | Klapper et al. | 604/264 |
| 5,328,470 A | * 7/1994 | Nabel et al. | 604/101.03 |
| 5,354,279 A | 10/1994 | Hofling | |
| 5,385,148 A | * 1/1995 | Lesh et al. | 600/471 |
| 5,419,777 A | * 5/1995 | Hofling | 604/264 |
| 5,672,174 A | * 9/1997 | Gough et al. | 606/41 |
| 6,102,926 A | * 8/2000 | Tartaglia et al. | 600/564 |
| 6,309,370 B1 | * 10/2001 | Haim et al. | 604/66 |

OTHER PUBLICATIONS

Goette et al., "Transcatheter Subendocardial Infusion", Circulation 1996; 94:1449–1455, American Heart Association, Inc.

Li et al., "Percutaneous transluminal gene transfer into canine myocardium in vivo by replication–defective adenovirus", Cardiovascular Research 30 (1995) 97–105.

* cited by examiner

Primary Examiner—Michael J. Hayes
Assistant Examiner—Roz GhaFoonàn
(74) Attorney, Agent, or Firm—Larson & Taylor PLC

(57) ABSTRACT

The multilumen catheter (2) is provided at one end with a needle system (9, 9') formed by two or more single-lumen needles which are provided with respective discharge openings (110, 111) and which, via their longitudinal lumina (10, 11), are connected to corresponding lumina (3, 4) of the catheter for separate release of a tracer fluid for external image diagnostics systems and therapeutic fluids, for example DNA plasmids. The needles may be both straight or both helical or one of these needles may be straight and the other needle may be helical.

15 Claims, 4 Drawing Sheets

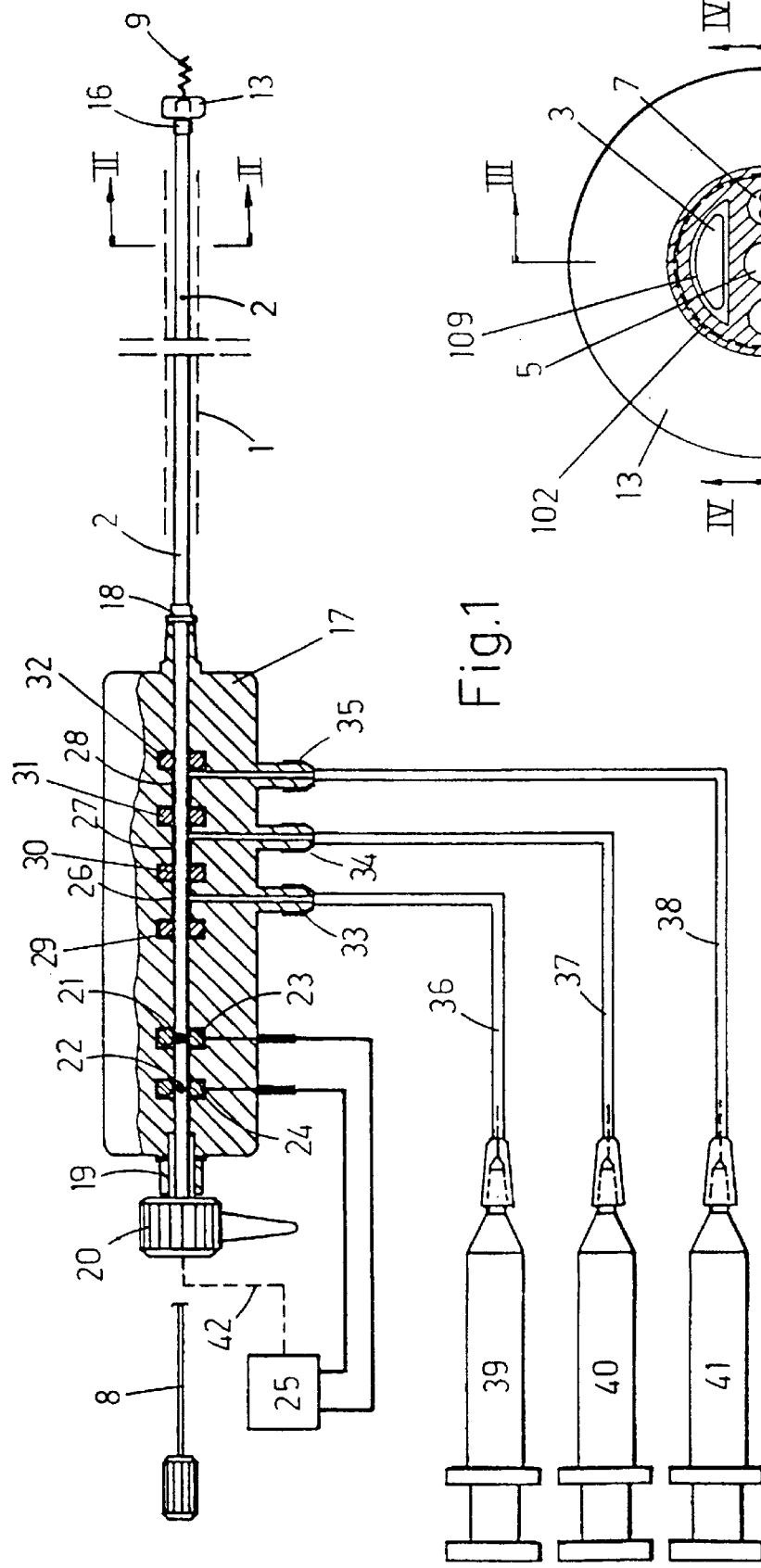
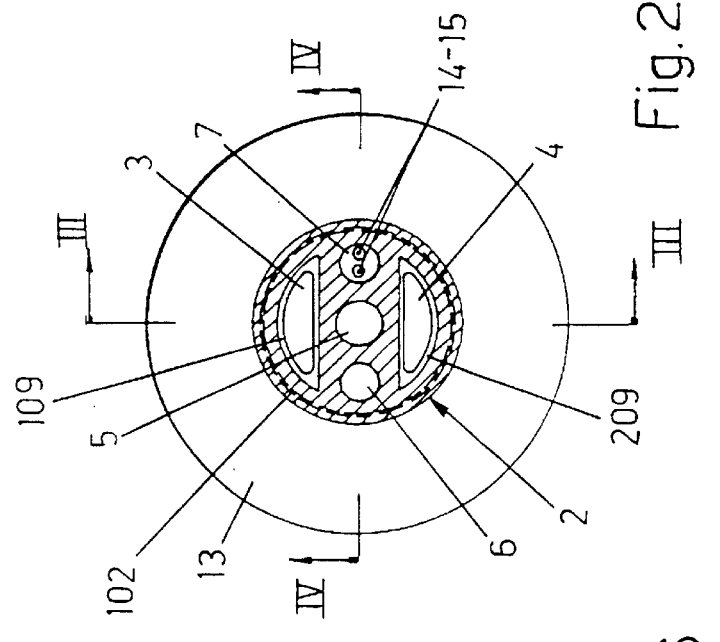
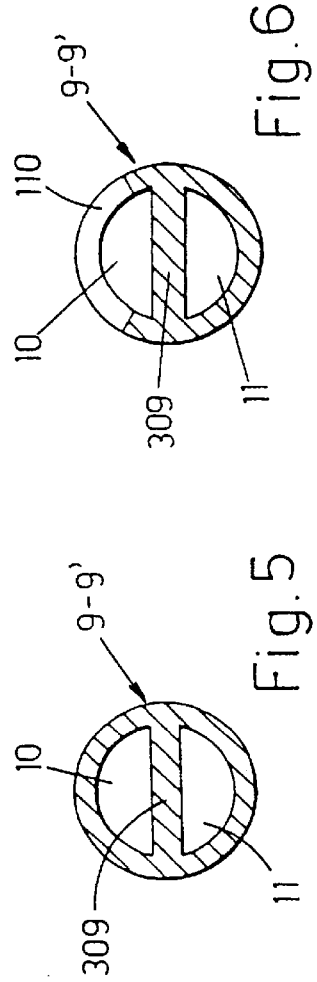

CATHETER SYSTEM FOR PERFORMING INTRAMYOCARDIAC THERAPEUTIC TREATMENT

BACKGROUND OF THE INVENTION

The invention relates to a method and the associated apparatus for performing intramyocardiac therapeutic treatment by means of the controlled infusion, in this anatomical location, of therapeutic fluids of varying nature and composition. With this method and apparatus it is possible to treat patients who suffer from cardiac ischaemia and who are not able to tolerate surgical therapy involving a coronary bypass or coronary angioplasty using catheters. At present there are many patients suffering from heart disease which is advanced to the point where it can no longer be treated using the solutions mentioned. Complete re-vascularization is not possible in 20% of the patients who undergo bypass surgery. The patients who cannot be treated with the abovementioned solutions belong, for example, to the following categories: patients with extensive heart disease affecting the distal vessels; patients with symptomatic ischaemia resulting from a diseased vessel which is too small to be bypassed; patients who do not have adequate ducts for bypassing; patients with total chronic occlusion and with distal vessels which are small and/or cannot be viewed.

A new therapy which is currently becoming more widespread for the treatment of this type of patient consists in the percutaneous injection, into the cardiac muscle, of genic substances, for example DNA plasmids, which induce the formation of new blood vessels. At least six different carrier systems have been used for genic transfer to the heart muscle cells, namely: DNA devoid of viral or physical adjuvants which increase the genic release; DNA encapsulated in modified liposomes; DNA complexed with cationic liposomes; retroviral carriers; adeno-associated viral carriers. This therapy is currently performed by making a small incision in the chest in order to inject the abovementioned plasmids into the myocardium, continuously monitoring the patient by means of transoesophageal echocardiography in order to check the movement of the cardiac wall during the percutaneous injection, in order to prevent the plasmid being injected into the blood, inside the cavity of the left-hand ventricle. The recent clinical experiments involving injection of plasmids into the myocardium, during surgical treatment or a mini-thoracotomy, are very interesting, but are unable to solve many problems when this procedure is used as the one and only therapy, in particular problems relating to optimization of the most suitable site for injection and the number and dosing of the intramyocardial injections. It is also obvious that the surgical solution limits very much the possibility of performing multiple treatment or treatment which is repeated over time.

It was thought that a catheter system suitable for the intramyocardiac injection of plasmids may be able to overcome the limitations of the present surgical solution indicated above.

According to the publication "Percutaneous Transluminal Gene Transfer into Canine Myocardium in Vivo by Replication-Defective Adenovirus" Jian Jun Li et. al. (Cardiovascular Research 1995: 30: 97–105), previous experiments involving the percutaneous injection of genes into the myocardium of dogs, by means of adenovirus, were performed using an injection catheter composed of a catheter guide and a guided catheter, with a needle at its terminal end, inserted into the left-hand ventricle of the heart. Under a fluoroscope, the needle was inserted into the myocardium and its correct position of insertion was confirmed by suction of the blood. If the needle is inserted into the wall of the cardiac muscle, its lumen is closed by the muscle itself and therefore the suction of blood is prevented.

Various injection catheters have been studied in order to improve the injection of a drug into an area inside the human body. Injection catheters have for example been produced by Wilson Cook Medical Inc. (Cook Italia Sri), said catheters being specifically designed for the sclerotherapeutic endoscopic treatment of oesophageal varices. The Boston Scientific Corporation markets needles for liquid injection therapy using a dedicated twin-lumen catheter and associated extendable and retractable needle with an ample washing lumen for ensuring vision with an endoscope in bleeding conditions.

None of the catheters with injection needles proposed by the current technology has been specifically developed and can neither be adapted to solve the problem of percutaneous and transvascular injection of plasmids into the human myocardium. With a needle catheter of the known type it is difficult to maintain a fixed position inside the moving wall of the myocardium and it is therefore difficult to inject, in a reliable manner, plasmids into the said wall. Similar difficulties have been encountered with the catheters of pacemakers when they have to be positioned in a different point of the apex of the right-hand ventricle, for example in the interatrial or interventricular septum. In these cases, a helical electrode screwed into the wall of the endocardium, in order to ensure immediate stability of the implant pending the growth of tissue thereon, is used. The use of a helical and hollow electrode for the injection of liquids into the human body has been described in U.S. Pat. No. 5,431,649 for a purpose different from that of the present invention, namely for the hyperthermic treatment of neoplasia of the prostate and for treatment of myocardiac ablation by means of radiofrequency, using a perfusion of saline solution through the cavity of the helical electrode.

An important factor which prevents the use of the abovementioned catheter perfusion systems for the function in question is the fact that they are not able to provide a safe, reproducible and recordable method for demonstrating that the injection of the plasmids is performed in a selected area of the myocardium and not in the blood stream; in fact the aforementioned solution of confirming the position of the needle by suction is not suitable for this purpose on account of the high risk of false situations created by the closure of the needle lumen by blood clots.

A recent publication "Transcatheter Subendocardial Infusion. A Novel Technique for Mapping and Ablation of Ventricular Myocardium", Andreas Goette et. al. (Circulation 1996: 94: 1149–1455) described an infusion catheter equipped with an electrode corresponding to the injection needle located on the distal end of said catheter and provided with a second ring electrode in the vicinity of the same needle. Two lumina which are formed inside the catheter and by means of which it is possible to perform a sequential administration of fluid mixtures converge towards this needle. A tracer substance is injected via a lumen of the catheter in order to map, by means of fluoroscopy, the point of injection of the needle into the myocardium of the left-hand ventricle, while a fluid mixture with ethanol is subsequently injected through the second lumen of the catheter in order to perform a chemical ablation of a volume of the myocardium. By means of this method, with the associated catheter, it is possible to identify with reasonable certainty the area of the myocardium into which the needle is inserted, but the problems, as described in the abovementioned publication, resulting from the difficulty of keeping a straight needle in the correct position in a beating myocardium and preventing remixing between the fluids introduced through the two catheter lumina, the latter intercommunicating via the common lumen of the injection needle, cannot be solved. Owing to the inherent elasticity of the material from which lumina of the catheter may be made and the notable curvature to which the catheter itself is subject during insertion into the human body, it cannot be ruled out that the pressure exerted on a fluid which is to be injected may cause a partial transfer of this fluid from its lumen under pressure to the other lumen which is at a lower pressure, with the result of unexpected and constant mixing of the two fluids and possible limitation of the volume of the fluid actually injected into the myocardium, since a part of this fluid, instead of being discharged from the needle, flows back into the lumen of the catheter which is at a pressure less than that of the active lumen.

U.S. Pat. No. 5,354,279 ("Plural Needle Injection Catheter") envisages a catheter provided at its terminal end with a plurality of thin pre-formed metal needles emerging in a ray-like arrangement and designed to release pharmaceutical substances onto the arteries. The lumina of these needles communicate, however, with a single lumen of the catheter so that this apparatus may not be used for the purposes of the present invention, either.

By way of conclusion, the known art, with the procedures and the devices described based on a catheter system with injection needle, does not allow the practical realization of an apparatus and a method for injecting plasmids solely using the intramyocardiac method, owing to problems associated with the movement of the endocardium and the impossibility of separating completely injection of the therapeutic fluids from injection of the tracer fluid.

BRIEF SUMMARY OF THE INVENTION

The object of the invention is to solve these and other problems of the already known art by means of a catheter provided with two or more longitudinal lumina and provided at its terminal end with a multilumen needle system, each lumen of this needle system having its own discharge opening and being connected to a corresponding lumen of the catheter. The lumina of the catheter are connected to external systems for releasing separately tracer fluids for external image diagnostics systems by means of which it is possible to verify the correct position of the needle in the cardium tissue and release therapeutic fluids, for example DNA plasmids. The needle system in question may be formed by a multilumen needle or by several single-lumen needles arranged alongside each other and each connected to a corresponding lumen of the catheter.

BRIEF DESCRIPTION OF THE SEVERAL VIEWS OF THE DRAWINGS

Further characteristic features and advantages arising therefrom will appear more clearly from the following description of certain preferred embodiments thereof, illustrated purely by way of a non-limiting example in the accompanying sheets of drawings, in which:

FIG. 1 is an overall side view, with parts shown in cross section, of the catheter system according to a preferred embodiment of the invention;

FIG. 2 shows a cross section through the middle of the catheter, along the line 11—11 of FIG. 1;

FIGS. 5 and 6 are cross sections through the multilumen needle along the lines V—V and VI—VI of FIG. 3, respectively;

DETAILED DESCRIPTION OF THE INVENTION

Figure 3:
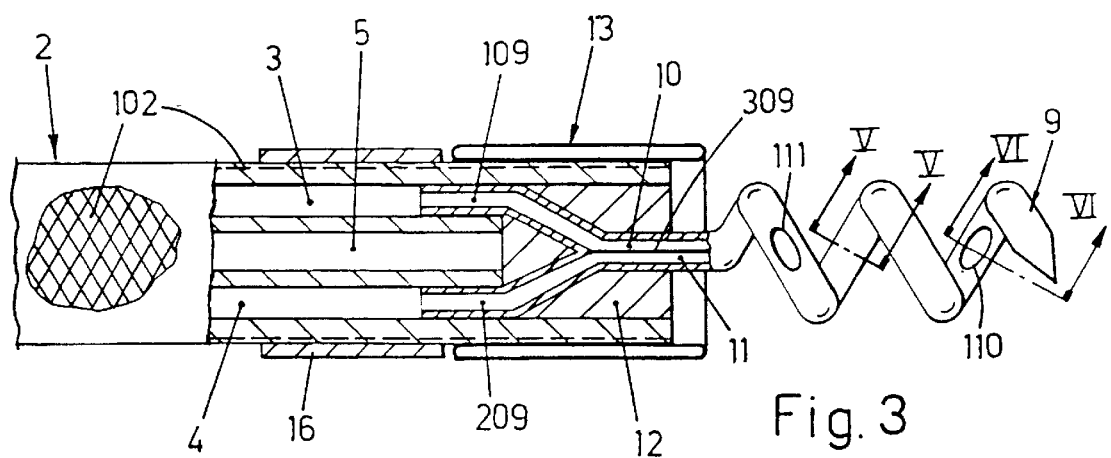
FIGS. 3 and 4 show further details of the end part of the catheter with a multilumen needle, which is sectioned respectively along the lines III—III and IV—IV of FIG. 2 and with parts being visible.

FIGS. 1 and 2 the numeral 1 designates schematically a catheter guide of the known type which is pre-formed or steerable and which is inserted into the blood circulation which leads to the left ventricle of the heart and inside which the catheter system in question is then inserted, said catheter system comprising a catheter 2 which has a suitable length and cross section and is made of any material suitable for this purpose, for example Polyimide, and is provided internally with a meshwork braiding 102 and/or other suitable means (see also FIG. 3) which allow a twisting torque to be applied to the said catheter, without the latter being deformed, such that a rotation applied to the front end of the catheter results in an identical rotation of the terminal end of this catheter. The catheter 2 is provided internally with several longitudinal lumina, for example a pair of main and opposite lumina 3 and 4, for example having a cross section in the form of a circle segment, and has between said lumina, in a symmetrical arrangement, arranged alongside each other and aligned along the diametral plane of the catheter, three secondary lumina 5, 6 and 7, for example with a round cross section, one of which is located preferably coaxially in the catheter, for receiving the guide spindle 8 which is of the type usually used for operating traditional pacing catheters.

Figure 3A:
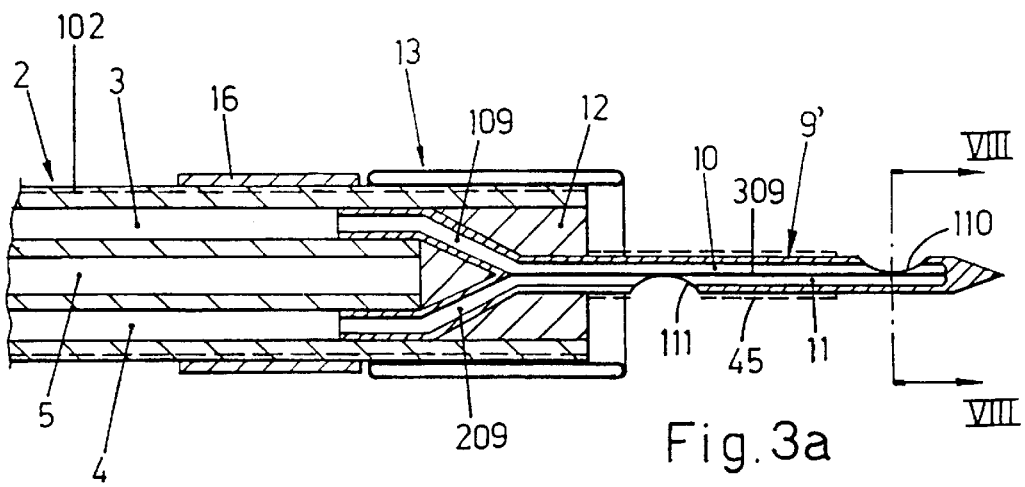
FIG. 3a is a variation of embodiment of the straight needle.
Figure 4:
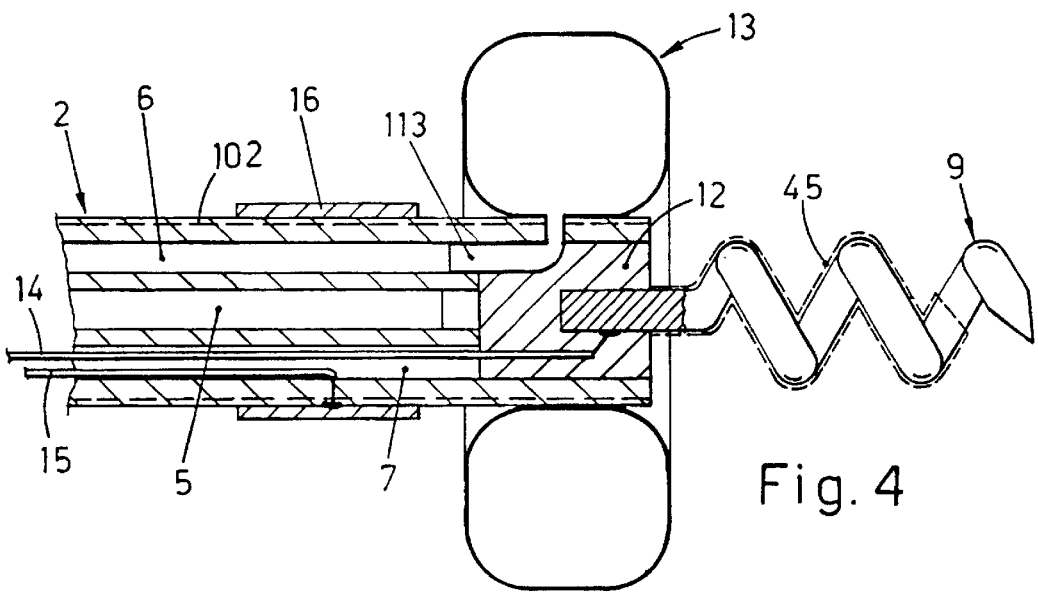

A multilumen needle system is fixed onto the terminal end of the catheter 2 by means of a special insert 12, in a position of longitudinal alignment with the said catheter, said needle system being formed by a needle which may be straight as indicated by 9' in FIG. 3a or may preferably have a cylindrical helical shape, as indicated for example by 9 in FIGS. 3 and 4. It is understood that the scope of the invention also includes helical needles other than that illustrated, for example which are of the straight type and have one or more external helices, for example similar to wood screws. From FIG. 5 it can be seen that the needle has two longitudinal lumina 10 and 11 which are arranged closely alongside each other and divided by a common wall 309 over the whole length of the body of this needle. The base of the needle has a fork-shaped configuration and the corresponding branches 109 and 209, which form a continuation of the respective lumina 10 and 11 of the said needle, are engaged in the corresponding lumina 3 and 4 of the catheter.

Both in the case of FIG. 3 and in the case of FIG. 3a, the internal lumina of the needle are provided with respective lateral discharge openings, one of which is indicated by 110 and is located at a short distance from the needle tip, while the other one indicated by 111 is located further upstream, in the middle part or at the base of the said needle (see also FIG. 6).

The terminal end of the catheter is provided with a retractable device, which is useful as an end-of-travel stop, for stopping penetration of the needle 9 or 9' into the wall of the myocardium which has to be treated. For this purpose it may be possible to use a torus-shaped balloon 13 which is made of impermeable and flexible material and which is fixed laterally onto the terminal end of the catheter 2 and has at least one internal duct 113 which passes through the insert 12 and is designed to engage into one of the secondary lumina of the catheter, for example into the lumen 6 (FIG. 2).

From FIG. 4 it can be seen that the end of an electrical conductor 14 which runs along the whole length of the catheter and is housed inside one of the secondary lumina, for example the lumen 7 in FIG. 2, is connected to the body of the needle 9 or 9', together with an optional additional electrical conductor 15 connected to an optional ring 16 which is made of electrically conducting material and is fixed on the outside of the terminal end of the catheter and is useful as a reference electrode for the various operations where the needle acts as a conductor of electrical impulses. The conductors 14 and 15 are suitably insulated from each other. If the braiding 102 of the catheter is made of an electrically conducting material, it may replace either one of the said electrical conductors 14 or 15. It is understood that the function of reference electrode may be performed by means other than the ring 16 mentioned above, for example using solutions known in the sector of cardiac electro-stimulation.

From FIG. 1 it can be seen that the initial section of the catheter passes through the body of a distributor 17 with respect to which the said catheter may rotate, but not move axially, for example owing to the presence of end stops 18 and 19. The knob 20 by means of which a rotation may be imparted to the said catheter is fixed onto the front end of the catheter, whereas, with regard to that stated above, the distributor 17 may remain at a standstill. The front ends of the electrical conductors 14 and 15 are connected to small electrically conducting rings 21 and 22 which are fixed externally to different points of the catheter body, are insulated with respect to each other and with which brushes 23 and 24 of the distributor 17 co-operate, said brushes being in turn connected via respective conductors to a composite, external, fixed apparatus 25, which will be described in greater detail below.

The lumina 3, 4 and 6 of the catheter are closed at the outer front end and are provided along the section which passes through the distributor 17 with respective radial openings which are situated at mutually distant points of the catheter and lead into respective annular chambers 26, 27 and 28 of said distributor and which are insulated from each other and from the exterior by annular sealing gaskets 29, 30, 31 and 32. These chambers lead to cable connectors 33, 34 and 35 to which flexible pipes 36, 37, 38 may be connected, said flexible pipes being provided at the other end with Luer connectors to which syringes 39, 40, 41 may be connected, the first thereof being useful, for example, for injecting or drawing liquid into/from the balloon 13, i.e. for filling it and activating it as shown in FIG. 4 or for reducing it into the collapsed condition as shown in FIG. 3, while the syringe 40 is useful for example for injecting tracer liquid which will emerge, for example, from the opening 111 of the needle 9 or 9', and the syringe 41 is used, for example, for injecting DNA plasmids which for example will be discharged from the end opening 110 of the said needle.

The catheter system as described functions and is used in the following manner. After positioning the catheter guide 1 in the patient, the catheter 2 is inserted inside said guide by means of the special guide spindle 8. The end balloon 13 is in the collapsed condition. After insertion of the catheter, the balloon 13 is activated by means of the syringe 39 and, by means of the external knob 20, the catheter itself is rotated in the direction for screwing of the helical needle 9 into the myocardium, until this needle has been completely screwed in. The correct position of the needle may be verified from the outside by means of the apparatus 25 which detects, for example, a bioelectrical impedance and/or ECG, using the electrical conductor 14 connected to the needle and the conductor 15 connected to the annular reference electrode 16. In order to improve the results of this test, the needle 9 or 9' may be advantageously lined with a thin layer of electrically insulating material, for example, Parylene, over practically the whole length, as schematically indicated by the broken lines and by 45 in FIGS. 3a and 4, except for an appropriate tip portion which remains electrically conducting.

Once screwing of the needle into the myocardium has been performed, via the syringe 40, a correct quantity of tracer is injected into this wall and, if the needle is correctly inserted, remains for a relatively long period of time in the said wall and may be easily detected by external image diagnostics systems of the known type, in the form of a persistent spherical-shaped mark. Should the needle not be correctly inserted into the myocardium, the injected tracer would become dispersed in the blood stream. The injected tracer may for example be of the type which is useful for detection by means of X-rays or using ultrasound image or magnetic nuclear resonance systems. If a dual-lumen needle as shown in FIGS. 3 and 3a is used, the tracer fluid is preferably discharged from the orifice 111 of the needle itself since, if it is subsequently established using the abovementioned procedure that the needle is correctly inserted in the myocardium, there is the absolute certainty that the other discharge orifice 110, intended for the discharge of therapeutic fluid, is also correctly inserted into the myocardium itself.

After verifying and documenting with appropriate means that the needle has been correctly inserted, DNA plasmids are injected into the myocardium via the syringe 41. In order to reinforce the transfer of the abovementioned plasmids into the cells of the cardiac tissue, the external apparatus 25 may be arranged so as to transmit into the tissue itself, via the electrical circuit connected to the needle 9, electrical impulses which have suitable characteristics and are synchronized with the beat R of the spontaneous activity of the heart. Again for this purpose, the external apparatus 25 may be designed to generate ultrasounds which are conveyed to the needle 9 and therefore to the perfused zone of the myocardium, via a conductor with suitable characteristics, which is indicated schematically in FIG. 1 by 42 and which is for example connected to the needle via the axial lumen 5, after removal of the guide spindle 8. It is understood that the catheter may have a secondary lumen specifically designed to contain an ultrasound conductor connected to the needle 9 or 9'.

Figure 7:
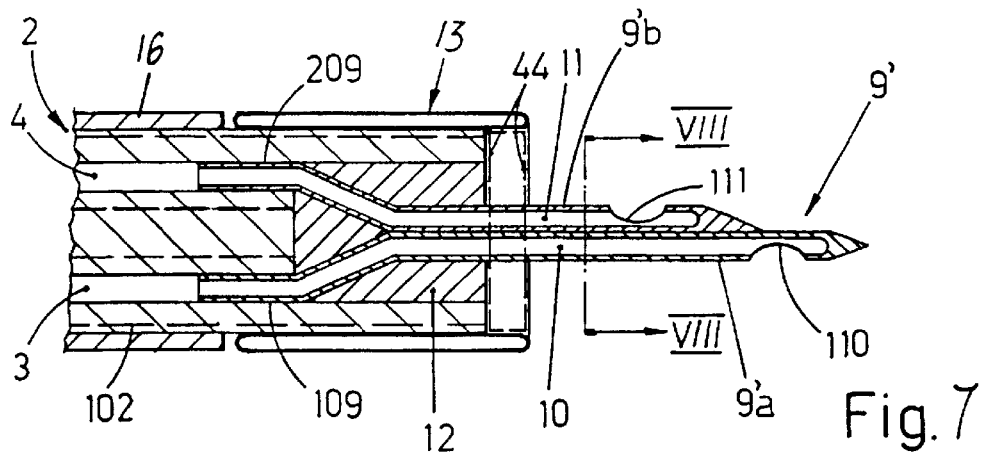
FIG. 7 shows, longitudinally sectioned, the end part of a multilumen catheter, with the multilumen needle system being formed by two single-lumen and straight needles arranged alongside each other.
Figure 9:
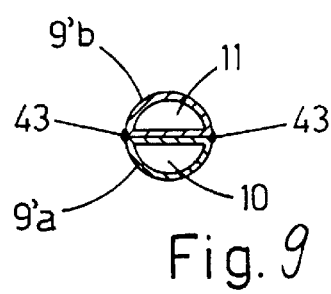
FIGS. 8 and 9 show possible cross sections through the needles of the needle system according to FIG. 7, sectioned along the line VIII—VIII.
Figure 8:
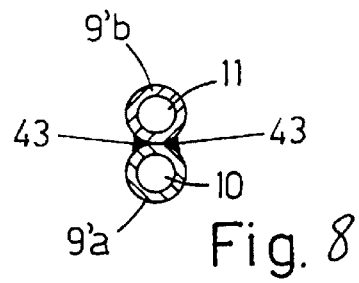

With reference to FIGS. 7 to 16, variations of embodiment of the needle system mounted on the catheter will now be described, said catheter, unlike the one previously considered, being composed of two single-lumen needles. The catheter 2 illustrated in FIG. 7 is identical to the multilumen catheter illustrated in FIG. 1 and its lumina 3 and 4, which are respectively connected to the external systems for injection of the therapeutic fluid and the tracer fluid, are joined to the end sections 109, 209 of respective straight and single-lumen needles 9'$a$ and 9'$b$ which are preferably of different length, preferably arranged in axial alignment with the catheter and preferably fixed together by means of welds 43, as can be seen from FIGS. 8. 10 and 11 indicate the lumina of the needles which terminate in respective openings 110, 111 for discharging the fluids conveyed by said lumina. The tip of the shorter needle is preferably shaped in the manner of a flute mouth-piece and is suitably connected to the side surface of the adjacent needle in order to facilitate penetration, into the myocardium, of the needle system 9' thus formed. FIG. 9 illustrates a variation according to which the needles 9'$a$ and 9'$b$ have a flattened—for example semi-circular—cross section so that the needle system 9' formed by them can be made to assume a substantially round cross section.

In the solution according to FIGS. 10, 11 and 12, again relating to a needle system 9' of the straight type, the longer needle 9'$a$ is partly inside and coaxial with the shorter needle 9'$b$, the end part of which is closed, converging onto the needle 9'$a$, and may be provided with several lateral openings 111 for discharging the tracer fluid. The needle 9'$a$ emerges in a sealed manner from the needle 9'$b$ at the start of the bifurcation which forms the end sections 109 and 209 for connection to the lumina 3 and 4 of the catheter.

Figure 13:
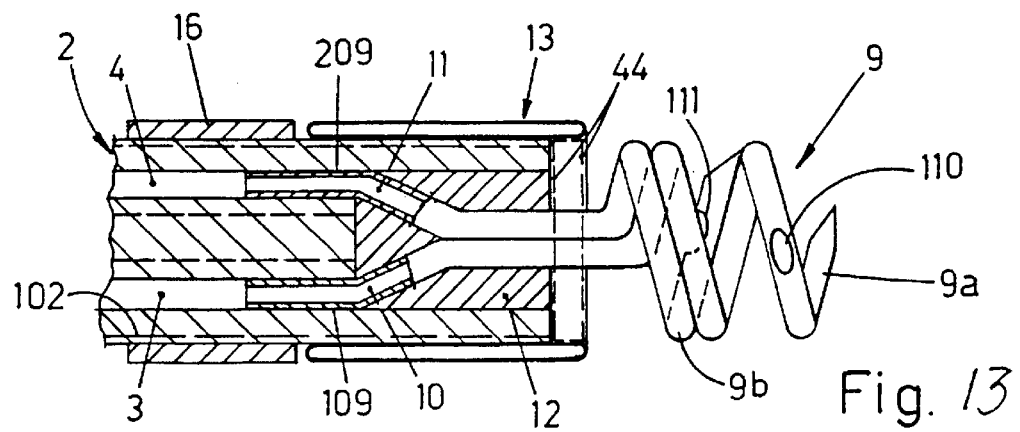
FIG. 13 shows, cross sectioned and with parts visible, a needle system formed by two helical needles arranged alongside each other.

The solution according to FIG. 13 is equivalent to that of FIG. 7, but envisages a needle system 9 which is formed by two helical needles 9$a$ and 9$b$ which are arranged alongside each other and preferably fixed by means of welding and which extend around the axis of the catheter 2. The comments made with reference to FIGS. 8 and 9 for the solution of FIG. 7 are also applicable here. The needles enter preferably into the catheter being closely arranged around its axis and then diverge away from each other and engage into the lumina 3, 4 with the end sections 109, 209. It is understood that the scope of the invention also includes the variant, not shown, whereby the helical needles 9$a$ and 9$b$ are staggered and distant from each other, with the tip of the shorter needle being distant from the body of the longer needle. In this case the needles may enter into the catheter with sections which are distant from the axis of the said catheter.

Figure 10:
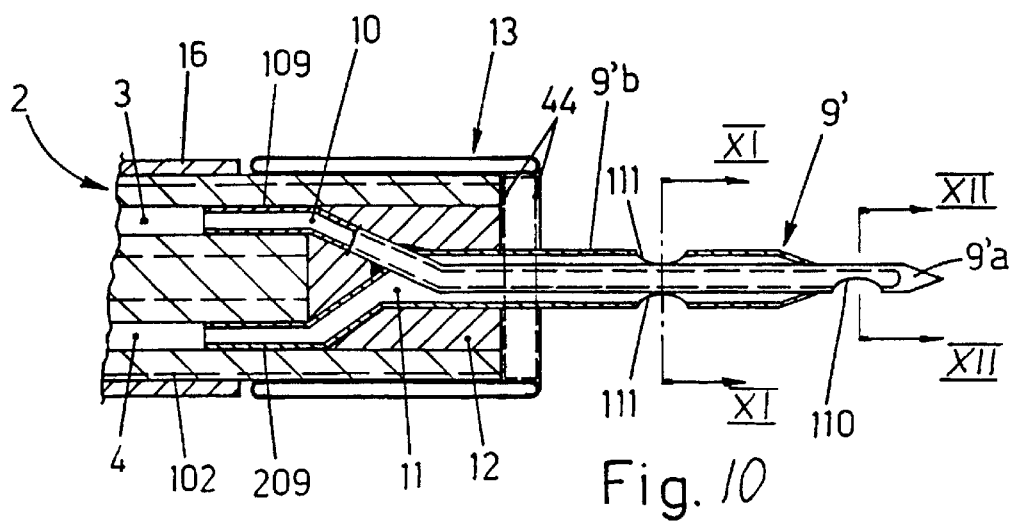
FIG. 10 shows, cross sectioned and with parts visible, a needle system formed by two straight and coaxial needles.
Figure 11:
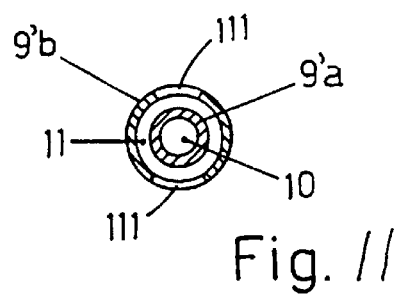
FIGS. 11 and 12 show details of the needle system according to FIG. 10, sectioned along the lines XI—XI and XII—XII, respectively.
Figure 12:
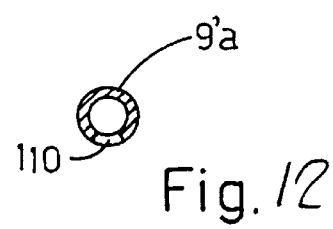
Figure 14:
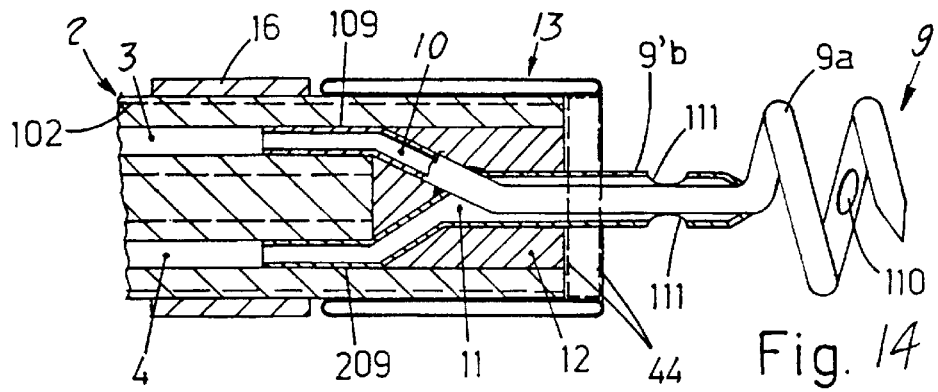
FIG. 14 shows, cross sectioned and with parts visible, a needle system formed by two straight needles coaxial with each other and of different length and with the projecting needle portion having a helical shape.

The solution according to FIG. 14 is derived from that of FIG. 10 and envisages a needle system 9 formed by a short needle 9'$b$ of the straight type from which a needle 9$a$ terminating in a helical shape projects coaxially.

Figure 15:
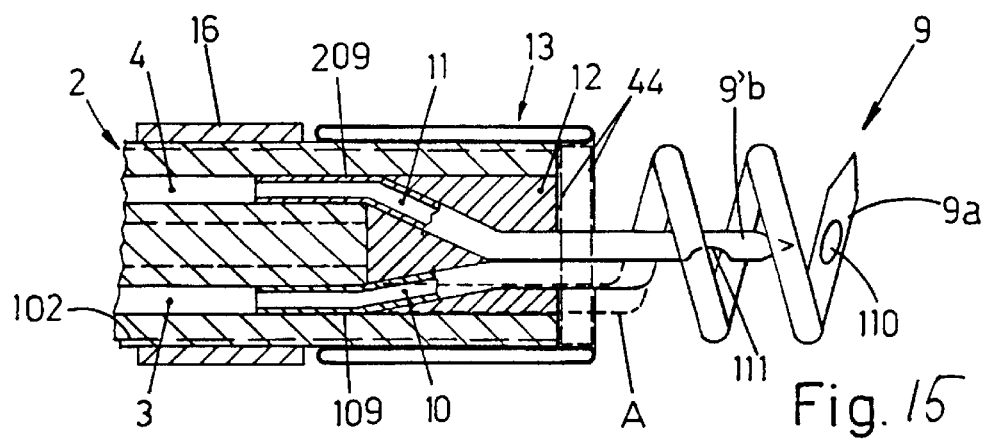

The solution according to FIG. 15 illustrates a needle system 9 formed by a straight short needle 9'$b$ which is aligned axially with the catheter and by a long helically shaped needle 9$a$ which extends concentrically around the said central needle 9'$b$.

Figure 16:
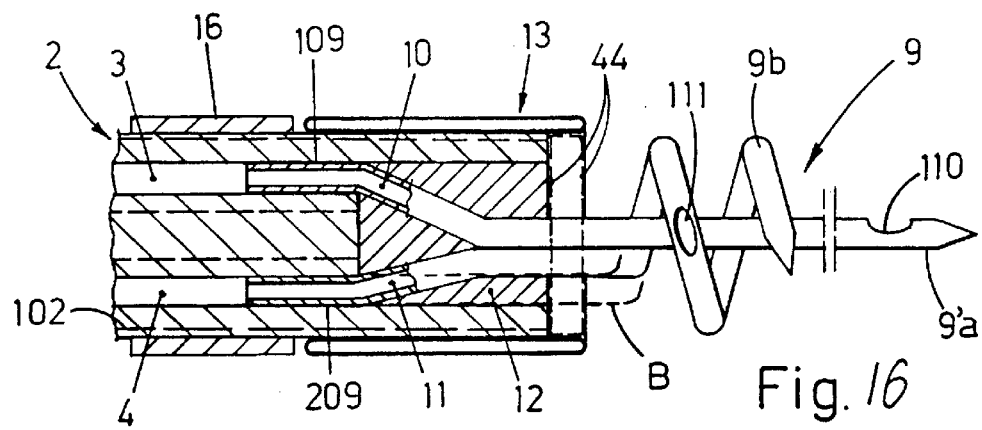
FIGS. 15 and 16 show, cross sectioned and with parts visible, further needle systems formed by a straight axial needle circumscribed by a helical needle which may be, respectively, projecting or retracted with respect to the said axial needle.

The solution according to FIG. 16 is a variation of the solution according to FIG. 15 and envisages a needle system 9 formed by a long straight central needle 9'$a$ and by a helically shaped external needle 9$b$ which extends concentrically around the said central needle. This solution could be preferred to that of FIG. 15 since the straight central needle 9'$a$ is inserted firstly into the myocardium and acts as a centring element and a rotational pivot for the helical needle 9$b$. In both solutions according to FIGS. 15 and 16, the helical needle is able to enter into the catheter with an arrangement close to the straight needle, as illustrated by continuous lines, or is able to enter into the catheter with an arrangement offset from the axis of the straight central needle, as indicated by A and B, in order to favour, if necessary, automatic stopping of the screwing action of the needle system.

In FIGS. 7 to 16, 44 denotes in broken lines the location, if necessary, on the terminal end of the catheter, of an ultrasound generator which is integral with the base of one or both needles and connected to an electrical supply circuit, not shown, which passes through a secondary longitudinal lumen of the catheter for connection to an external power supply unit. With this solution it is possible to transmit to the needle system, and therefore to the perfused zone of the myocardium, the ultrasounds which are necessary for reinforcing the transfer of the therapeutic fluid into the cells of the myocardium tissue. It is understood that the same comments made in respect of the preceding solutions are applicable to the variations according to FIGS. 7 to 16, with regard to the possibility of electrical connection of the needle system to external apparatus and partial insulation of the said needle system, except for a suitable section of its terminal part, using electrical insulation material, for example based on "Parylene". The catheter will also be provided on the terminal end with the electrically conducting ring 16 having the function of a reference electrode for all the operations which the needle system performs as a conductor of electrical impulses. The catheter will also be provided with the internal anti-twisting braiding 102 and on the terminal end of the said catheter the already mentioned retractable device 13, with external activation and deactivation controls, for stopping penetration of the needle system into the myocardium will be provided.

It is understood that the dimensions and the proportions indicated in the drawings are purely exemplary and do not limit the scope of the invention. Purely by way of a non-limiting example, some dimensional characteristics for the construction of the apparatus according to the invention are now described. The catheter 2 may, for example, have an external diameter of about 7 French, that is to say about 2.1 mm, while the external diameter of the helix of the needle system with at least one helical needle, may for example be about 2 mm. The projecting part of the longer needle must not, for example, exceed the length of about 5 mm, while the projecting part of the shorter needle will have for example a length of about 2.5–3 mm. The needles which form the needle system may for example each have an external diameter of about 0.30 mm.

What is claimed is:

1. Method for intramyocardiac therapeutic treatment comprising the following operational steps:
    inserting into a desired chamber of a heart, with a preformed or steerable catheter guide, a catheter having
        a) first and second longitudinal catheter lumina,
        b) a terminal end, c) a multilumen needle system provided at the terminal end, the needle system including (i) a needle section extending longitudinally from the terminal end for insertion into a myocardium of the desired chamber and including first and second longitudinal needle lumina provided with respective first and second lateral discharge openings at different longitudinal positions along the needle section, wherein the first lateral opening of the first needle lumen is located closer to the terminal end of the catheter than the second lateral opening of the second needle lumen, and (ii) a base section which respectively connects the first and second needle lumina to the first and second catheter lumina , and d) first and second release systems which are connected respectively to the first and second lumina at external ends thereof, the first and second release systems functioning during operation to release into a desired zone inside the myocardium of the desired chamber respectively (i) a fluid for therapeutic treatment and (ii) a tracer fluid for external image diagnostics systems;

inserting the multilumen needle system into the myocardium at a desired point;

injecting the tracer fluid through the first lumen of the catheter and the first needle of the needle system and thus into the desired zone of the myocardium, wherein said injecting step includes a discharging of the tracer fluid through the first lateral opening of the multilumen needle system which is closest to the terminal end of the catheter;

checking and recording a total and correct insertion of the needle system into the desired point of the myocardium using the tracer fluid present thereat and the external image diagnostics system; and releasing, in the desired zone of the myocardium into which the multilumen needle system has been correctly inserted, the therapeutic fluid via the second lumina of the catheter and the second needle.

2. Method according to claim 1:

wherein the first lateral opening of the first needle lumen is located closer to the terminal end of the catheter than the second lateral opening of the second needle lumen; and wherein said injecting step includes a discharging of the tracer fluid through the first lateral opening of the multilumen needle system which is closest to the terminal end of the catheter.

3. Method according to claim 1:

wherein the needle section has a helical shape;

wherein the base section of the needle system includes an end-of-travel balloon which is activatable between an expanded and a retracted position about the base section; and wherein said step of inserting the multilumen needle system into the myocardium at the desired point comprises activating the end-of-travel balloon to the expanded position and then rotating of the catheter and the associated needle section of the helical shape.

4. Method according to claim 1, wherein said step of releasing the therapeutic treatment fluid comprises a release of carrier systems for performing genetic transfer to cells of the heart.

5. Method according to claim 1:

wherein the needle system includes an electrical conductor; and further including steps of (i) connecting the electrical conductor of the multilumen needle system to an external apparatus and (ii) generating electrical impulses with the external apparatus synchronized with a beat R of the heart to reinforce a transfer of the therapeutic fluid into the cells of the heart.

6. Method according to claim 1:

wherein the needle system also includes an ultrasound emitter; and further including a step of activating the ultrasound emitter associated with the needle system to reinforce a transfer of the therapeutic fluid into the cells of the heart.

7. Method according to claim 1:

wherein the needle system includes an electrical conductor; and further including a step of checking a state of penetration of the needle section of the multilumen needle system into the myocardium, said checking of the state of penetration including the steps of connecting the electrical conductor associated with the needle system to an external apparatus, and monitoring of an intramyocardiac electrocardiograph with the external apparatus.

8. Method according to claim 1:

wherein the needle system includes an electrical conductor; and further including a step of checking of the state of penetration of the needle section into the myocardium, said checking of the state of penetration including the steps of connecting the electrical conductor associated with the multilumen needle system to an external apparatus, and measuring an bioelectric impedance with the external apparatus.

9. Method according to claim 4, wherein the released therapeutic treatment fluid is DNA plasmids.

10. (Re-presented—formerly dependent claim #4) Method for intramyocardiac therapeutic treatment comprising the following operational steps:

inserting into a desired chamber of a heart, with a preformed or steerable catheter guide, a catheter having e) first and second longitudinal catheter lumina, f) a terminal end, g) a multilumen needle system provided at the terminal end, the needle system including (i) a needle section extending longitudinally from the terminal end for insertion into a myocardium of the desired chamber and including first and second longitudinal needle lumina provided with respective first and second lateral discharge openings at different longitudinal positions along the needle section, and (ii) a base section which respectively connects the first and second needle lumina to the first and second catheter lumina , and h) first and second release systems which are connected respectively to the first and second lumina at external ends thereof, the first and second release systems functioning during operation to release into a desired zone inside the myocardium of the desired chamber respectively (i) a fluid for therapeutic treatment and (ii) a tracer fluid for external image diagnostics systems;

inserting the multilumen needle system into the myocardium at a desired point;

injecting the tracer fluid through the first lumen of the catheter and the first needle of the needle system and thus into the desired zone of the myocardium;

checking and recording a total and correct insertion of the needle system into the desired point of the myocardium using the tracer fluid present thereat and the external image diagnostics system; and releasing, in the desired zone of the myocardium into which the multilumen needle system has been correctly inserted, the therapeutic fluid via the second lumina of the catheter and the second needle, wherein said step of releasing the therapeutic treatment fluid comprises a release of carrier systems for performing genetic transfer to cells of the heart.

11. Method according to claim 10:

wherein the needle section has a helical shape;

wherein the base section of the needle system includes an end-of-travel balloon which is activatable between an expanded and a retracted position about the base section; and wherein said step of inserting the multilumen needle system into the myocardium at the desired point comprises activating the end-of-travel balloon to the expanded position and then rotating of the catheter and the associated needle section of the helical shape.

12. Method according to claim 10:

wherein the needle system includes an electrical conductor; and further including steps of (i) connecting the electrical conductor of the multilumen needle system to an external apparatus and (ii) generating electrical impulses with the external apparatus synchronized with a beat R of the heart to reinforce a transfer of the therapeutic fluid into the cells of the heart.

13. Method according to claim 10:

wherein the needle system also includes an ultrasound emitter; and further including a step of activating the ultrasound emitter associated with the needle system to reinforce a transfer of the therapeutic fluid into the cells of the heart.

14. Method according to claim 10:

wherein the needle system includes an electrical conductor; and further including a step of checking a state of penetration of the needle section of the multilumen needle system into the myocardium, said checking of the state of penetration including the steps of connecting the electrical conductor associated with the needle system to an external apparatus, and monitoring of an intramyocardiac electrocardiograph with the external apparatus.

15. Method according to claim 10:

wherein the needle system includes an electrical conductor; and further including a step of checking of the state of penetration of the needle section into the myocardium, said checking of the state of penetration including the steps of connecting the electrical conductor associated with the multilumen needle system to an external apparatus, and measuring an bioelectric impedance with the external apparatus.

* * * * *